United States Patent [19]

Grubbs et al.

[11] Patent Number: 4,919,151
[45] Date of Patent: Apr. 24, 1990

[54] SYNTHETIC POLYMER FOR ENDOCAPSULAR LENS REPLACEMENT

[75] Inventors: Robert H. Grubbs, South Pasadena, Calif.; Robert J. Coots, Sheffield Lake, Ohio; Stanley H. Pine, South Pasadena, Calif.

[73] Assignee: California Institute of Technology, Pasadena, Calif.

[21] Appl. No.: 403,833

[22] Filed: Sep. 1, 1989

Related U.S. Application Data

[63] Continuation of Ser. No. 70,060, Jul. 6, 1987, abandoned.

[51] Int. Cl.⁵ ............................................. A61B 19/00
[52] U.S. Cl. ......................................... 128/898; 623/6
[58] Field of Search ............................. 623/6; 522/40; 128/897-899

[56] References Cited

U.S. PATENT DOCUMENTS

| | | | |
|---|---|---|---|
| 4,191,176 | 3/1980 | Spina et al. | 128/1 R |
| 4,327,450 | 5/1982 | Girard | 128/1 R |
| 4,543,398 | 9/1985 | Bany et al. | 526/279 |
| 4,638,040 | 1/1987 | Hammar | 526/279 |
| 4,673,539 | 6/1987 | Hammer et al. | 526/245 |

*Primary Examiner*—C. Fred Rosenbaum
*Assistant Examiner*—Sharon Rose
*Attorney, Agent, or Firm*—Ashen Golant Martin & Seldon

[57] ABSTRACT

A synthetic polymer (24) is provided for endocapsular lens (18) replacement in an eye (10). The polymer, whch is injected into the lens capsule (16) after removal of the lens, comprises an oxygen-stabilized photosensitive prepolymer. An example of such a prepolymer comprises polyether with urethane linkages with one or both ends capped with a functional group containing at least one double bond, such as an acrylate, a methacrylate, or a styrene.

The polymerization reaction is initiated with a photoinitiator such as dimethoxyphenylacetophenone and is quenched in the presence of oxygen. Contrary to the prior art polymers, the time of curing is on the order of only a minute or so. The viscosity and thickness of the polymer formed may be tailored to achieve a desired index of refraction of between about 1.3 and 1.6.

17 Claims, 1 Drawing Sheet

SYNTHETIC POLYMER FOR ENDOCAPSULAR LENS REPLACEMENT

This is continuation of co-pending application Ser. No. 07/070,060 filed on July 6, 1987, abandoned.

TECHNICAL FIELD

The present invention relates to treatment of defects in the eye, and, more particularly, to the replacement of diseased or otherwise defective eye lenses.

BACKGROUND ART

Surgery on the eye is becoming more commonplace and sophisticated as new techniques and devices are developed to combat impaired sight or even blindness. One such field of surgery is the replacement of the lens in the eye which can be necessitated, for example, by cataract development, which opacifies the lens.

Procedures have been developed for removal of the lens. Early procedures have involved the removal of the lens and lens capsule (transparent membrane encapsulating the lens) by means of forceps or suction. More recently, less traumatic means have been developed; such means involve particulating the lens, an example of which is called sonication, which involves ultrasonic disintegration of the lens by application of high frequency vibrations thereto. The lens fragments are then removed by aspiration.

Replacement of the lens to avoid requiring the patient to wear spectacles with massive lenses has been investigated. Some solutions have included injecting a viscous liquid or a silicone into the vacant lens capsule. Implantation of intraocular lenses has also been done, but the implant is rigid and not focusable and is easily dislodged by shock or vibration.

More recently, G. M. Wright and T. D. Talcott in U.S. Pats. 4,537,943; 4,542,542; and 4,608,050 have disclosed injection by needle of a polymer composition into the lens capsule. The polymeric composition comprises a silicone prepolymer, a cross-linker and a platinum-based catalyst. The composition cures in the lens capsule to an optically clear, gel-like material which may accommodate, or focus, through action of the eye lens muscle.

However, a problem with the polymeric composition disclosed by the prior art is that a separate heating step is required to permit removal of the needle from the eye to initiate polymerization at the injection site and thus prevent loss of polymer therefrom. Further, the time of initial cross-linking is on the order of several hours, which involves lengthy immobilization of the eye to permit complete curing.

Thus, what is required is a polymeric composition providing the advantages of the prior art while avoiding most, if not all, the problems associated with the prior art approaches.

DISCLOSURE OF THE INVENTION

In accordance with the invention, a synthetic polymer is provided for endocapsular lens replacement. The polymer, which is injected into the lens capsule after removal of the lens, comprises an oxygen-stabilized photosensitive prepolymer. An example of such a prepolymer comprises a polyether with urethane linkages with one or both ends capped with a functional group containing at least one double bond, such as an acrylate, methacrylate, or a styrene.

The polymerization reaction is initiated by light using a photoinitiator such as dimethoxyphenylacetophenone and other aryl ketones and is quenched in the presence of oxygen. Contrary to the prior art polymers, the time of curing is on the order of only a minute or so. The viscosity and thickness of the polymer formed may be tailored to achieve a desired index of refraction.

BEST MODES FOR CARRYING OUT THE INVENTION

Figure 1:
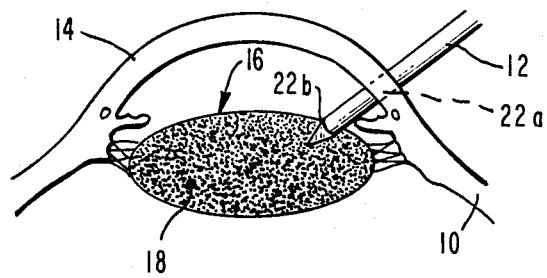
FIGS. 1–5 are diagrammatic views of a portion of an eye, showing the procedure of lens removal, followed by injection of the polymer used in the method of the invention.
Figure 2:
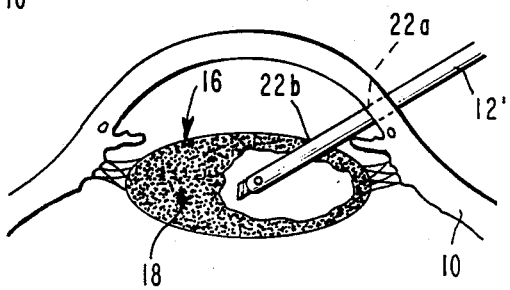
Figure 3:
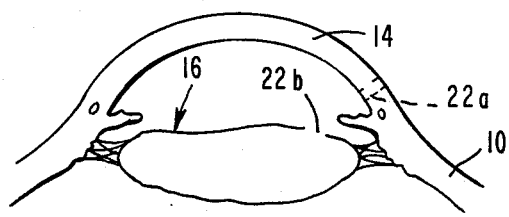

Referring now to the drawings, wherein like numerals designate like elements throughout, a portion of an eye 10 is shown, with a probe 12 inserted through the cornea 14 and the lens capsule 16 into the lens 18. As shown in FIG. 1, the probe, which advantageously comprises means for emitting high frequency vibrations, has caused ultrasonic disintegration of the lens 18 by a process known as sonication. In FIG. 2, the probe 12, which also includes aspiration means 12', has begun removal of the denatured protein of the lens, or lens fragments, 18. In FIG. 3, the process is complete, leaving behind the empty lens capsule 16. The particular method of disintegrating the lens and removing it is immaterial to the practice of the invention, and thus forms no part of this invention.

Figure 4:
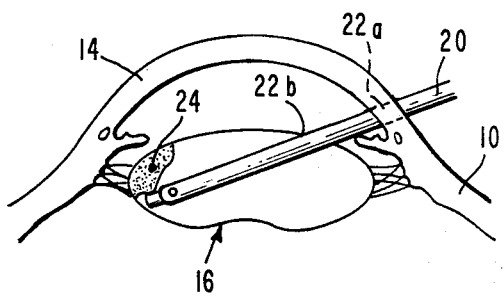

In FIG. 4, a needle 20 is inserted into the same incision 22 used by the probe 12 and is used to inject a polymer composition 24 into the lens capsule 16. The polymer is deoxygenated prior to injection.

Figure 5:
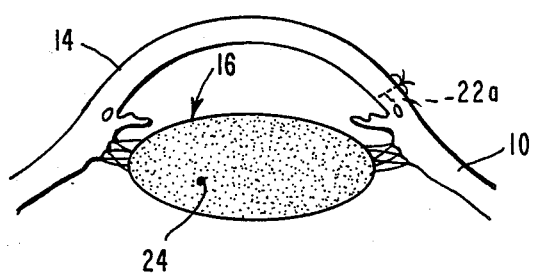

The needle 20 is gradually withdrawn as the polymer fills the capsule 16 and the incision 22a through the cornea 14 is surgically closed. Since the polymer cures to its final state within a matter of minutes using light, no heating step is required to cure the polymer around the incision 22b in the lens capsule 16 to permit removal of the needle 20. The completely filled lens capsule 16 is depicted in FIG. 5.

The polymer composition 24 is injected into the lens capsule 16 through slit 22b, which is typically no larger than 3 mm, and is intended to cross-link rapidly so that the composition, which is injected in a liquid state, will not squirt out the slit when the needle 20 is withdrawn.

The polymer composition used in the practice of the invention comprises (a) a prepolymer and (b) a photoinitiator. The prepolymer is preferably one that is substantially linear, with one, and preferably both, ends capped with a functional group having at least one olefinic bond. Examples of such functional groups include acrylates, methacrylates, and styrenes.

It is preferred that both ends be capped, in order to form a more homogeneous polymer. The presence of the double bond permits olefinic-type cross-linking.

Examples of suitable prepolymers include polypropylene glycols, polypropylene glycols with polyethylene glycol units, polybutylene glycols with polyethylene glycol units, urethanes, and silicones such as dimethyl silicone and ethyl silicone. The molecular weight of the prepolymer advantageously ranges from about 2,000 to 8,000, although lower or higher molecular weight material may be employed.

The photoinitiator comprises a composition which initiates polymerization of olefinic end groups in the visible-to-near-UV region. Examples of such photoinitiators, particularly suited for causing cross-linking of acrylate groups, include acetophenone derivatives, such as dimethoxyphenylacetophenone.

The procedure for formation and removal of lens fragments 18 involves the use of a microscope and a lamp for illumination of the eye. When injecting the polymer composition 24 into the lens capsule 16, the cross-linking procedure may be performed using the same lamp employed in conjunction with the microscope used by the surgeon to remove the lens fragments 18. This lamp is of the appropriate wavelength and is of sufficient intensity to activate the photoinitiator and begin the process of cross-linking. The concentration of photoinitiator is normally about 0.25 to 2 wt %.

The time for reaction is ordinarily less than about five minutes. The observable physical properties do not seem to change after the first several minutes of cross-linking.

The photoinitiator is quenched by the presence of oxygen, and accordingly, the operation may be done by continuously flushing the eye with an inert gas, such as nitrogen or argon, or with saline until the reaction is substantially complete.

The prepolymer is stabilized with oxygen during storing and sample preparation and degassed in the dark before injection, such as with a vacuum pump, and back-filled with the inert gas. Normal atmosphere is sufficient to stabilize the prepolymer during handling and storage.

It is well-known that the eye lens is layered, like that of an onion, with each layer having a different refractive index. The polymerized composition is essentially homogeneous. However, the viscosity and refractive index of the composition is a function of the uncapped portion of the prepolymer, and may be configured to provide a refractive index between about 1.3 and 1.6.

Since the polymerized composition 24 is an elastomer, the muscles of the eye 10 may still perform their normal function of accommodation. Further, the ability to tailor the polymerized composition in terms of elasticity, viscosity and refractive index means that the lens formation, when done in conjunction with the sonication lens removal, may be performed early in the process of cataract formation.

EXAMPLES

Polyether glycols of average molecular weights between 1,000 and 4,000 were combined through urethane linkages using diisocyanates such as isophorone diisocyanate (Fluka Chemical Corp., Hauppauge, NY) or methylene bis (4-cyclohexyldiisocyanate) (Mobay Chemical Corp., Pittsburgh, PA). The ends were then capped with a compound containing a terminal alkene such as isocyanatoethyl methacrylate (Dow Chemical Co., Midland, MI) or 2-hydroxyethyl methacrylate (Aldrich Chemical Co., Milwaukee, WI). Reactions were catalyzed by a tin compound such as stannous dioctanoate.

The resultant prepolymer was a colorless liquid with viscosity sufficiently low so that it could be injected by syringe through a 20 gauge needle. The material could be purified, if necessary, through various known chromatographic methods. BHT (25 to 100 ppm) may be added to stabilize the polymer.

The polymer was thoroughly mixed with the appropriate quantity of photoinitiator, such as 2,2-dimethoxy-2-phenyl acetophenone (Aldrich Chemical Co.), transferred to a syringe, then pumped in vacuo, protected from light, for at least 24 hours. The polymer-filled syringe was stored, protected from light, under an inert atmosphere.

The Table below lists various polymer formulations prepared pursuant to the foregoing teachings.

TABLE

| No. | Polyether glycol; g | Diisocyanate linker; g | Catalyst | End cap; g | Photoinitiator; % |
|---|---|---|---|---|---|
| 1 | Voranol (1965); 8.8 | IPDI; 0.76 | Sn(Oc)$_2$ | IEM; 0.29 | DMPA; 0.3 |
| 2 | Voranol (1965); 10.7 | IPDI; 0.95 | " | IEM; 0.28 | DMPA; 0.25 |
| 3 | Voranol (3829); 20.1 | IPDI; 0.58 | " | IEM; 0.73 | DMPA; 0.3 |
| 4 | Voranol (3829); 10.0 | IPDI; 1.1 | " | HEA; 0.69 | DMPA; 1.2 |
| 5 | PPG-4000; 11.6 | DesW; 1.4 | " | HEM; 0.75 | DMPA; 1.0 |
| 6 | PPG-4000; 11.6 | DesW; 1.4 | " | HEA; 0.67 | " |
| 7 | PPG-4000; 8.9 | IPDI; 0.93 | " | HEA; 0.50 | " |
| 8 | PPG-3000; 9.0 | IPDI; 1.0 | " | HEM; 0.31 | " |
| 9 | PPG-3000; 9.0 | IPDI; 1.0 | " | HEA; 0.27 | " |
| 10 | Terethane (650); 15.0 | — | " | IEM; 7.1 | " |

Legend:
Voranol (1965) - Polypropylene glycol end capped with 12% ethylene oxide; MW = 1,965
Voranol (3829) - Polypropylene glycol end capped with 22% ethylene oxide; MW = 3,829
PPG-4000 - Polypropylene glycol; MW = 4,000
PPG-3000 - Polypropylene glycol; MW = 3,000
Terethane (650) - Polytetramethylene glycol; MW = 650
IPDI - Isophorone diisocyanate
DesW - Desmodur W [methylene bis(4-cyclohexylisocyanate)]
Sn(Oc)$_2$ - Stannous dioctanoate
IEM - Isocyanatoethyl methacrylate
HEA - 2-Hydroxyethyl acrylate
HEM - 2-Hydroxyethyl methacrylate
DMPA - 2,2-Dimethoxy-2-phenylacetophenone Several of the foregoing polymers (Nos. 1, 2, 5, 6, 7) were injected into lens capsules of rabbits. Photo cross-linking was promoted by the visible light used to illuminate the surgical procedure. The polymer was stabilized in the lens shape within 1 to 2 minutes and reaction was complete within 5 minutes.

The mechanism for the photoinitiation apparently involves homolytic cleavage of the initiator to give two radicals, which then initiate the cross-linking reaction. Because molecular oxygen reacts with radicals, deoxygenation of the monomer allows for rapid cross-linking.

The resultant in situ cross-linked polymer was a transparent plastic with variable elasticity, depending on the degree of cross-linking and chemical composition.

Thus, a method of endocapsular lens replacement by forming a synthetic polymer in the lens capsule of an eye after removal of the lens has been disclosed. The method comprises injecting a photosensitive prepolymer into the lens capsule in the absence of oxygen. It will be clear to one of ordinary skill in the art that various changes and modifications of an obvious nature may be made without departing from the spirit of the invention, and all such changes and modifications are considered to be within the scope of the invention, as defined by the appended claims.

What is claimed is:

1. A method of endocapsular lens replacement by forming a synthetic polymer in the lens capsule of an eye after removal of the lens comprising:

(a) injecting a polymer composition comprising a photo-sensitive prepolymer and a photoinitiator into said lens capsule in the absence of oxygen;

(b) exposing said composition to light to form said synthetic polymer; and (c) curing said polymer within several minutes.

2. The method of claim 1 wherein said polymer is cured at ambient temperature.

3. The method of claim 2 wherein said photoinitiator comprises an acetophenone derivative.

4. The method of claim 3 wherein said photoinitiator comprises dimethoxyphenylacetophenone.

5. The method of claim 2 wherein said photoinitiator is present in an amount ranging from about 0.25 to 2 wt %.

6. The method of claim 2 wherein said photoinitiator is activated by exposure to visible-to-near-UV radiation.

7. The method of claim 1 wherein said prepolymer is stabilized against polymerization with oxygen prior to said injecting.

8. The method of claim 1 wherein said prepolymer is substantially linear, with at least one end capped with a functional group having at least one olefinic bond.

9. The method of claim 8 wherein said functional group is one selected from the group consisting of acrylates, methacrylates, and styrenes.

10. The method of claim 9 wherein said functional group comprises methylacrylate.

11. The method of claim 8 wherein said prepolymer comprises a composition selected from the group consisting of urethanes, polypropylene glycols, polypropylene glycols with polyethylene glycol units, polybutylene glycols with polyethylene glycol units, and silicones.

12. A method of endocapsular lens replacement by forming a synthetic polymer in the lens capsule of an eye after removal of the lens comprising:

(a) injecting a polymer composition comprising a photosensitive prepolymer and a photoinitiator comprising an acetophenone into said lens capsule in the absence of oxygen, said prepolymer comprising a polyether having both ends capped with an acrylate group and stabilized against polymerization with oxygen prior to said injecting;

(b) exposing said composition to light to form said synthetic polymer; and (c) curing said polymer within about five minutes.

13. The method of claim 12 wherein said polymer is cured at ambient temperature.

14. The method of claim 12 wherein said photoinitiator comprises dimethoxyphenylacetophenone.

15. The method of claim 14 wherein said photoinitiator is present in an amount ranging from about 0.25 to 2 wt %.

16. The method of claim 14 wherein said photoinitiator is activated by exposure to visible-to-near-UV radiation.

17. The method of claim 12 wherein said functional group comprises methylacrylate.

* * * * *